United States Patent [19]
Leboulch et al.

[11] Patent Number: 5,928,914
[45] Date of Patent: Jul. 27, 1999

[54] METHODS AND COMPOSITIONS FOR TRANSFORMING CELLS

[75] Inventors: Philippe Leboulch, Cambridge, Mass.; Eric Bouhassira, Hastings on Hudson, N.Y.; Karen Westerman, Reading, Mass.; Ken Julian Takekoshi, Bethesda, Md.

[73] Assignees: Albert Einstein College of Medicine of Yeshiva University, a Division of Yeshiva University, Bronx, N.Y.; Massachusetts Institute of Technology, Cambridge, Mass.

[21] Appl. No.: 08/743,796

[22] Filed: Nov. 5, 1996

Related U.S. Application Data

[63] Continuation of application No. 08/664,084, Jun. 14, 1996, abandoned.

[51] Int. Cl.$^6$ .......................... C12N 15/52; C12N 15/64; C12P 21/02; C07H 21/04
[52] U.S. Cl. .................. 435/172.3; 435/69.1; 435/70.1; 435/183; 435/320.1; 536/23.1
[58] Field of Search ............................ 435/172.3, 370.1, 435/183, 69.1, 70.1; 536/23.1

[56] References Cited

U.S. PATENT DOCUMENTS

| | | | |
|---|---|---|---|
| 4,959,317 | 9/1990 | Sauer | 435/172.3 |
| 5,434,066 | 7/1995 | Bebee et al. | 435/172.3 |

FOREIGN PATENT DOCUMENTS

| | | |
|---|---|---|
| 0300422 | 1/1989 | European Pat. Off. . |
| WO9706271 | 9/1990 | WIPO . |
| WO9309239 | 5/1993 | WIPO . |

OTHER PUBLICATIONS

Abremski et al. (1983), "Studies on the Properties of P1 Site–Specific Recombination: Evidence for Topologically Unlinked Products Following Recombination", *Cell* 32:1301–1311.
Argos et al. (1986), "The Integrase Family of Site–Specific Recombinases: Regional Similarities and Global Diversity", *The EMBO Journal* 5:433–440.
Hoess et al. (1982), "P1 Site–Specific Recombination: Nucleotide Sequence of the Recombining Sites", *Proc. Natl. Acad. Sci. USA* 79:3398–3402.
Hoess et al. (1990), "The Cre–lox Recombination System", *Nucleic Acids and Molecular Biology* 4:99–109.
Sauer (1993), "Manipulation of Transgenes by Site–Specific Recombination: Use of Cre Recombinase", *Methods in Enzymology* 225:890–900.
Sauer et al. (1988), "Site–Specific DNA Recombination in Mammalian Cells by the Cre Recombinase of Bacteriophage P1", *Proc. Natl. Acad. Sci. USA* 85:5166–5170.
Schlake et al. (1994), "Use of Mutated FLP Recognition Target (FRT) Sites for the Exchange of Expression Cassettes at Defined Chromosomal Loci", *Biochemistry* 33:12746–12751.
Waterhouse et al. (1993), "Combinatorial Infection and In Vivo Recombination": A Strategy for Making Large Phage Antibody Repertoires, *Nucleic Acids Research* 9:2265–2266.
Wang, P. et al. (1995), "High Frequency Recombination Between LOXP Sites In Human Chromosomes Mediated By an Adenovirus Vector Expressing CRE Recombinase", *Somatic Cell and Molecular Genetics* 21(6):429–441.
Choulika, A. et al. (1996), "Transfer of Single Gene–Containing Long Terminal Repeats Into The Genome of Mammalian Cells By A Retroviral Vector Carrying the CRE Gene and the LOXP Site", *Journal of Virology*, 70(3):1792–1798.
Leboulch, P. et al. (1996), "Retrovirus and Cre–Lox–mediated Integration (RCLI): A two–step gene transfer procedure for efficient chromosomal integration of large DNA fragments", Abstract No. 2379, Thirty–eighth Annual Meeting of the American Society of Hematology, Orlando, Florida, USA, Blood 88 (10 Suppl. 1 Part 1–2), 688A.
Bouhassira, E.E. et al. (1996), "Recombinase–mediated––cassette–exchange (RMCE): A novel technique for integration of single copy of transgenes at pre–determined chromosomal sites. Application to the study of the human beta–globin LCR", Abstract No. 749, Thirty–eighth Annual Meeting of the American Society of Hematology, Orlando, Florida, USA, Blood 88 (10 Suppl. 1 Part 1–2), 190A.
Bergemann et al. "Exclusion of Specific DNA Sequences from integrated Retroviral Vectors . . . " NAR 23(21) 4451–4456, 1995.
Anton et al "Sie–Specific Recombination Mediated by an Adenovirus vector . . . " J. Virol 69 (8) 4600–4606, 1995.

*Primary Examiner*—Nancy Degen
*Attorney, Agent, or Firm*—Lahive & Cockfield, LLP; Jane E. Remillard, Esq.

[57] ABSTRACT

Methods and compositions for transforming cells, resulting in efficient and stable site-specific integration of transgenes, are disclosed. Transformation is achieved by introducing into a cell an acceptor vector, preferably a retroviral vector, which integrates into the genome of the cell. The acceptor vector comprises two incompatible lox sequences, L1 and L2. A donor vector is then introduced into the cell comprising a transgene flanked by the same L1 and L2 sequences. Stable gene transfer is initiated by contacting the lox L1 and L2 sequences with Cre recombinase.

24 Claims, 3 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: single
      (D) TOPOLOGY: linear    (ii) MOLECULE TYPE: DNA    (xi) SEQUENCE DESCRIPTION: SEQ ID NO:1:

ATAACTTCGT ATAATGTATG CTATACGAAG TTAT      34

(2) INFORMATION FOR SEQ ID NO:2:

(i) SEQUENCE CHARACTERISTICS:
      (A) LENGTH: 34 base pairs
      (B) TYPE: nucleic acid
      (C) STRANDEDNESS: single
      (D) TOPOLOGY: linear    (ii) MOLECULE TYPE: DNA    (xi) SEQUENCE DESCRIPTION: SEQ ID NO:2:

ATAACTTCGT ATAATGTATA CTATACGAAG TTAT      34

METHODS AND COMPOSITIONS FOR TRANSFORMING CELLS

This application is a Continuation of U.S. application Ser. No. 08/664,084 filed on Jun. 14, 1996 now abandoned.

GOVERNMENT FUNDING

The United States government may have rights to this invention pursuant to NIH grants.

BACKGROUND OF THE INVENTION

The success of gene therapy techniques depends largely on the ability to achieve a combination of stable chromosomal integration and high-level, regulated expression of transferred genes. Regulated gene expression is most easily achieved by means of large DNA fragments containing extensive cis-acting regulatory regions. For example, gene therapy for β-globin disorders may require high-level, position-independent expression of extended gene and LCR sequences.

Many current techniques allow efficient transient transfection of cells in vitro and in vivo with large DNA fragments. However, subsequent chromosomal integration is very inefficient. To overcome low levels of integration, retroviral vectors which integrate very efficiently in permissive cells can be used. However, such vectors are greatly limited by constraints of size and sequence composition.

U.S. Pat. No. 4,959,317 (Sauer et al.) disclose the use of Cre-Lox site-specific recombination to achieve gene transfer in eukaryotic cells. However, the system described does not provide efficient or stable integration of transferred DNA into the host genome (see e.g., (Sauer et al. (1993) *Methods in Enzymology* 225: at 898). This is largely due to the fact that excision of transferred DNA out of the genome, by way of intramolecular exchange, predominates over integration of DNA into the genome, by way of intermolecular site-specific recombination.

A site-specific DNA recombination system which allows for highly efficient and stable integration of transgene sequences into genomic DNA would be greatly beneficial.

SUMMARY OF THE INVENTION

The present invention provides methods and compositions for causing efficient and stable site-specific DNA recombination using a recombinase/lox system, such as the Cre/lox system. In one embodiment, the method comprises contacting a recombinase (e.g., Cre) with (a) an acceptor vector comprising two incompatible lox sequences, L1 and L2, and (b) a donor vector comprising a selected DNA flanked by the L1 and L2 sequences, or sequences which are compatible with the L1 and L2 sequences, thereby causing transfer of the selected DNA from the donor vector into the acceptor vector by recombination at the compatible lox sequences. In a preferred embodiment, the acceptor vector is a retroviral vector or an adeno-associated vector.

In another embodiment, the invention provides a method of transforming a cell with a selected DNA comprising, in any order, the steps of introducing into the cell an acceptor vector which integrates into the genome of the cell, the acceptor vector comprising two incompatible lox sequences, L1 and L2, (b) introducing into the cell a donor vector comprising the selected DNA flanked by the L1 and L2 sequences, or sequences which are compatible with the L1 and L2 sequences, and (c) contacting L1 and L2 with a recombinase, such as Cre, thereby causing transfer of the selected DNA from the donor vector into the acceptor vector. The recombinase can be introduced into the cell in the form of a protein or a gene encoding the protein.

In another embodiment, the invention provides a vector selected from the group consisting of retroviral vectors and adeno-associated vectors comprising two incompatible lox sequences, L1 and L2.

The methods and compositions of the invention can be used in methods of in vivo and In vitro gene transfer (e.g., gene therapy) to cause efficient and stable integration of transgene sequences.

DETAILED DESCRIPTION OF THE INVENTION

The present invention provides methods and compositions for causing efficient site-specific DNA recombination, for example, in methods of transforming cells. The advantages over current cell transformation techniques provided by the invention include highly efficient and stable integration of large DNA sequences, such as transgene sequences, into chromosomal DNA.

In one embodiment, the method of the invention comprises contacting a recombinase, such as Cre, with (a) an acceptor vector comprising two incompatible lox sequences, L1 and L2, and (b) a donor vector comprising a selected DNA flanked by the L1 and L2 sequences, or lox sequences which are compatible with the L1 and L2 sequences, thereby causing transfer of the selected DNA from the donor vector into the acceptor vector by recombination at the compatible lox sequences.

The term "site-specific recombination," refers to DNA transfer from a donor vector to an acceptor vector.

The term "lox sequence" refers to a nucleotide sequence which undergoes recombination (e.g., DNA cross-over and exchange) when catalyzed by a recombinase, such as Cre or another member of the Int family of recombinases (Argos et al. (1986) *EMBO J.* 5: 433).

The term "recombinase" refers to any recombinase capable of catalyzing a site-specific recombination at a lox site.

The term "incompatible lox sequences" refers to two or more lox sequences (referred to herein as L1 and L2) which differ from one another and, therefore, can not undergo recombination with one another. For example, lox sequences can be rendered incompatible if their nucleotide sequences differ by even one nucleotide, particularly in their spacer regions. In contrast, the term "compatible lox sequences" refers to two or more lox sequences which can recombine when catalyzed to do so by a recombinase.

The term "acceptor vector" refers to any vector capable of integrating into the genome of a cell. In a preferred embodiment, the acceptor vector is of viral origin, such as a retroviral vector or adeno-associated vector. Generally, the acceptor vector contains an exchange cassette (i.e., DNA which is replaced by DNA from the donor vector) and can also, optionally, contain a selectable marker gene.

The term "donor vector" refers to any vector (e.g., circular plasmid DNA) containing DNA which is transferred to the acceptor vector. Generally, the donor vector comprises plasmid DNA and, optionally, can contain a selectable marker gene.

Figure 1:
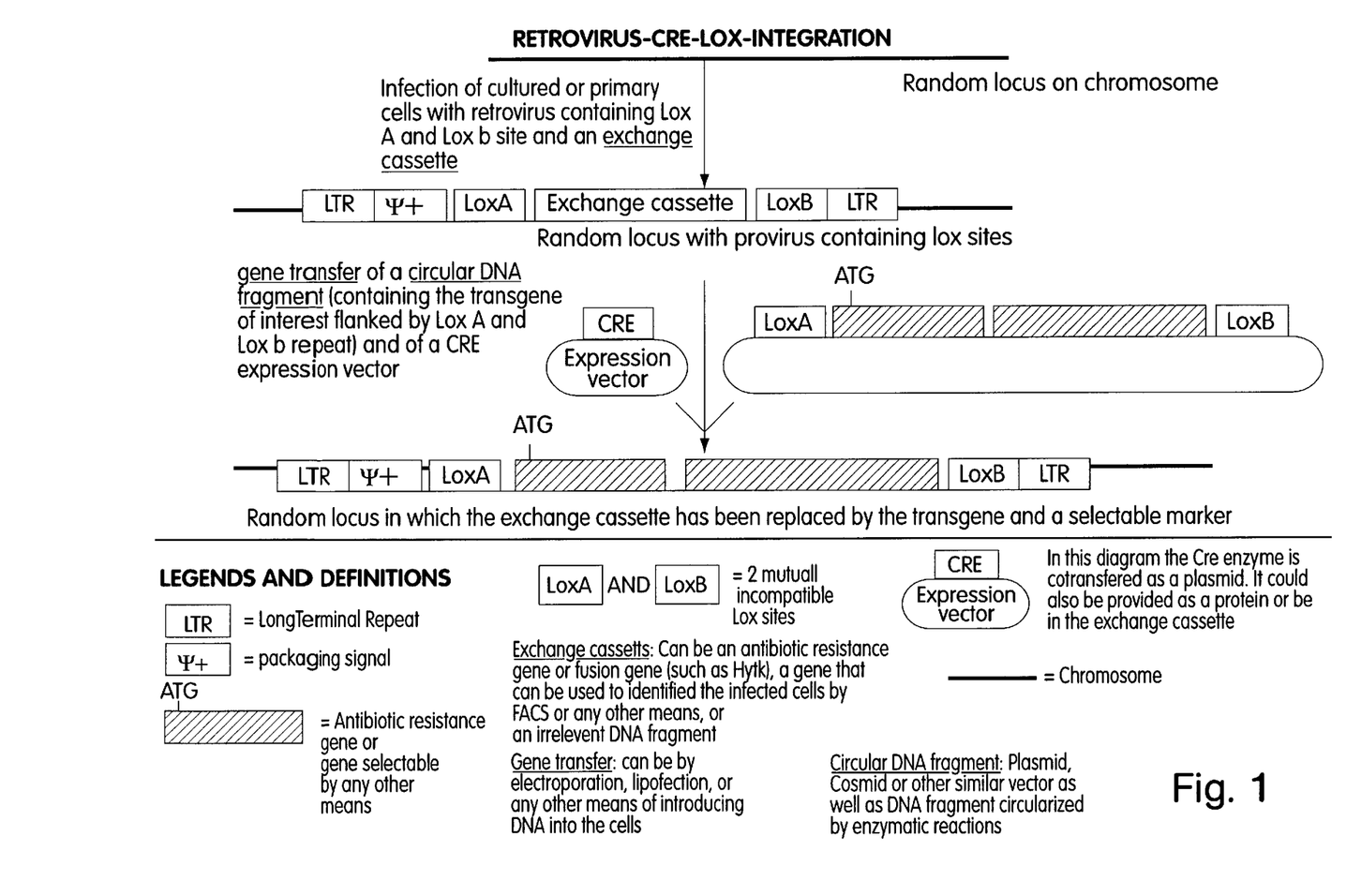
FIG. 1 is a schematic illustration of Cre/lox mediated gene transfer. Lox A and Lox B are mutually incompatible lox sites which are unable to recombine with each other in the presence of Cre recombinase.

The method of the present invention utilizes a recombinase mediated exchange reaction which takes place between identical or compatible (i.e., able to recombine with one another) lox sequences. The efficient exchange of DNA between identical or compatible lox sequences enables transfer of DNA from the donor to the acceptor vector, which each contain identical or compatible lox sites (see FIG. 1). However, once transferred from donor to acceptor vector (i.e., intermolecular transfer), the transferred DNA is "locked" into place due to the incompatibility of the two lox sequences (e.g., L1 and L2) within the acceptor vector which prevent intramolecular exchange and excision of the transferred DNA. Therefore, the transferred DNA is integrated in a highly stable manner.

In addition to effective and stable DNA exchange reactions, the methods of the present invention take advantage of highly efficient integration vectors, such as retroviral vectors, adeno-associated vectors, or vectors encoding retroviral integrases, for use as acceptor vectors. The studies described herein demonstrate that such vectors are compatible for use with site-specific DNA transfer systems, such as recombinase/lox systems.

Overall, the site-specific recombination system of the invention provides a means for highly efficient and stable DNA transfer which can be used, for example, in methods of gene therapy. For example, the methods and compositions of the present invention can be used to achieve a 100 to 10,000 fold increase in transgene integration and expression compared to random integration which occurs in the absence of site-specific recombination.

Accordingly, in another embodiment, the invention provides a method of transforming a cell, such as a mammalian cell, with a selected DNA. The method comprises the steps of (a) introducing into the cell an acceptor vector comprising two incompatible lox sequences, L1 and L2, (b) introducing into the cell a donor vector comprising the selected DNA flanked by the L1 and L2 sequences, or lox sequences which are compatible with the L1 and L2 sequences, and (c) contacting L1 and L2 with a recombinase, such as Cre, to cause transfer of the selected DNA from the donor vector into the acceptor vector (by way of an exchange reaction between the compatible lox sequences). While not essential, the acceptor vector is preferably introduced into the cell prior to introduction of the donor vector, so that the acceptor vector has integrated into the host genome prior to DNA exchange with the donor vector.

The acceptor vector can be any vector capable of being taken up by cells and integrating into genomic DNA. Preferred acceptor vectors include viral vectors which transfect cells directly, such as recombinant retroviruses, adenoviruses, adeno-associated virus, and herpes simplex virus-1. A prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a mutated subunits of the mALDH of the invention rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ΩCrip, ΩCre, Ω2 and ΩAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464).

Another preferred acceptor vector is an adenovirus-derived vector. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art.

Yet another viral vector system useful as the acceptor vecto is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as few as 300 base pairs of AAV can be packaged and can integrate.

Other viral vector systems that may be used as the acceptor vector in the methods of the present invention include herpes virus, vaccinia virus, and several RNA viruses.

The donor vector can be any vector (e.g., circular DNA) capable of being taken up by cells, either in vivo or in vitro, and capable of carrying the desired transfer (i.e., donor) DNA sequence. Suitable donor vectors include cosmids or DNA plasmids, such as recombinant bacterial or eukaryotic plasmids. The donor vector can be introduced into the host cell either in vivo or in vitro using a variety of known methods. For in vitro delivery, suitable methods include direct injection of the plasmid, $CaPO_4$ precipitation, electroporation, cationic lipofection, or use of artificial viral envelopes. For in vivo delivery, suitable methods include intravenous, intraperitoneal and intramuscular injection of the vector. The vector can also be targeted for delivery to selected cells (see e.g., U.S. Pat. No. 5,166,320).

To determine efficient uptake by cells, the acceptor, donor, or acceptor and donor vectors can, optionally, contain a marker gene, such as an antibiotic resistance gene or gene selectable by other means. The marker gene can be promoterless so that it will only be expressed when integrated into the acceptor vector containing a promoter to drive its expression.

The donor and acceptor vectors each contain at least two incompatible locks sequences ("L1 and L2") so that intramolecular recombination can not occur. At the same time, the locks sequences of the donor and acceptor vectors must be able to recombine intermolecularly (e.g., L1 with a compatible L1, and L2 with a compatible L2) with one another to allow DNA exchange between the donor and acceptor vectors. In order to ensure intermolecular exchange between compatible lox sequences, the lox sequences are generally oriented in the same direction.

Incompatibility between locks sequences can be achieved, for example, by way of mutating or modifying (e.g., by nucleotide addition, deletion or substitution) one of two identical lox sequences, preferably in their spacer sequences, so that the sequences differ. Testing to determine which mutations confer incompatibility can be performed using standard mutation assays which test for the ability of the mutated and non-mutated lox sequences to recombine.

In a preferred embodiment, one of the two incompatible lox sequences is the Lox P1 sequence of the Cre/lox system of bacteriophage P1 (Hoess et al. (1990) "Nucleic Acids and Molecular Biology," Vol 4, p. 99) having the sequence shown in SEQ ID NO:1. The Lox P1 sequence is a 34 base pair sequence which can be isolated from bacteriophage P1 by methods known in the art (see e.g., Hoess et al. (1982) *PNAS* 79:3398). The Lox P1 sequence consists of two 13 base pair inverted repeats separated by an eight base spacer sequence. Lox P1 sites can also be isolated from plasmids available from the ATCC (e.g., ATCC 53254 and 20773). Other suitable lox sequences include the Lox B, Lox L, and Lox R sequences isolatable from *E. coli* (Hoess et al. (1982), supra.). Lox sequences can also be chemically synthesized using known techniques, such as those described in the Examples below.

Accordingly, the other incompatible lox sequence can be a mutated form of the LoxP1 sequence, for example, having a point mutation in the eight nucleotide spacer sequence. In one embodiment, the point mutation is substitution of A for G at position 7 of the eight base spacer sequence of the wild type Lox P1 sequence, referred to herein as the Lox511 sequence (SEQ ID NO:2). Accordingly, in one embodiment, the two incompatible lox sequences of the invention have the following sequences:

*USA* 85:5166–5170). The recombinase or recombinase gene can be introduced or transfected into the host cell before, simultaneously, or following introduction of the donor and acceptor vectors.

In one embodiment, the recombinase gene (e.g., Cre) is contained in an expression vector which is co-transfected with the donor vector following introduction and integration of the acceptor vector into the host cell. In another embodiment, the recombinase gene is contained within either the acceptor vector or the donor vector. As with the donor vector, the recombinase gene can be introduced into the host cell either in vivo or in vitro using known techniques, such as $CaPO_4$ precipitation, electroporation, cationic lipofection, use of artificial viral envelopes, direct injection (e.g., intravenous, intraperitoneal or intramuscular). The vector can also be targeted for delivery to selected cells (see e.g., U.S. Pat. No. 5,166,320).

The DNA which is transferred from the donor to the acceptor vector by way of the site-specific recombination method of the invention can be any DNA desired for stable integration into a host cell genome. For example, the gene can be any transgene useful, for example, in gene therapy or for diagnostic purposes. The gene can encode a desired therapeutic protein, such as α, β or δ globin, blood coagulation factors (e.g., Factors VIII and IX) gene, cell surface receptors and other desirable proteins, for example, to correct inherited deficiencies of these proteins in an individual.

Accordingly, the methods and compositions of the invention can be used for a variety of therapeutic and diagnostic applications which require stable and efficient integration of transgene sequences into genomic DNA of cells. The methods and compositions can be used to transform a wide variety of eukaryotic cells (e.g., mammalian) cells and provide the advantage of high efficiency DNA transfer.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references and published patent applications cited throughout this application are hereby incorporated by reference.

EXAMPLES
MATERIALS AND METHODS
DNA Construction and Cell Culture

DNA vectors were made using standard techniques (Sambrook, J. et al. (1989) *Molecular Cloning: A Labora-*

```
              SPACER
Lox P1  ATAACTTCGTATA ATGTATGC TATACGAAGTTAT (SEQ ID NO:1)
Lox 511 ATAACTTCGTATA ATGTATAC TATACGAAGTTAT (SEQ ID NO:2)
```

Intermolecular recombination between compatible lox sequences in the donor and acceptor vectors is catalyzed by a recombinase, such as Cre or another member of the Int family of recombinases (Argos et al. (1986) *EMBO J.* 5:433) which have been shown to perform efficient recombination at lox sequences in both bacteria and in eukaryotic cells (Sauer et al. (1993) *Methods in Enzymology* 225:890–900). The recombinase can be introduced into the cell along with the donor and acceptor vectors in the form of a protein or as an expressible gene encoding the protein (e.g., the Cre gene described by Sauer, B. et al. (1988) *Proc. Natl. Acad. Sci.*

*tory Manual*—2nd ed. Cold Spring Harbor Laboratory Press, Cold Spring Harbor, New York, USA). Oligonucleotides were synthesized by Research Genetics, Inc. Accuracy of DNA construction was verified by sequencing. LXSN retroviral vector (Miller, A. D. et al. (1989) *Biotechniques* 7:980–990) was provided by D. Miller (Fred Hutchinson Cancer Research Center, Seattle), Hygromycin B (Lupton, S. D. et al. (1991) *Mol. Cell. Biol.* 11:3374–3378) phosphotransferase gene by D. Housman (MIT, Cambridge), Herpes Simplex virus thymidine kinase (HSV-TK) gene (Lupton, supra) by M. R. Capecchi (Salt Lake City, Utah), U19

SV40T mutant gene (Renfranz, P. J. et al. (1991) *Cell* 66:713–729) by R. D. McKay (MIT, Cambridge) and G. Almazan (McGill University, Montreal), Cre recombinase gene (Sauer, B. et al. (1988) *Proc. Natl. Acad Sci. USA* 85:5166–5170) by D. W. Ow (UC Berkeley, Albany), CD24 (Pawlink, R. et al. (1994) *Blood* 84:2868–2877). MSCV (murine stem cell virus) retroviral vector (Hawley, P. G. et al. (1994) *Gene Therapy* 1:136–138), pBabe retroviral vector (Morgenstern, J. P. et al. (1990) *Nucl. Acies Res.* 18:3587–3596) by R. Weinberg (MIT, Cambridge), pcDNA1 by Invitrogene Corp. and pOPRSVICAT by Stratagene, Inc. NIH3T3 cells were obtained from the ATCC, BOSC23 cells (Pear, W. S., et al. ((1993) *Proc. Natl. Acad. Sci., USA* 90:8392–8396) W. Pear and D. Baltimore (Rockefeller University, New York).

NIH3T3 cells were grown at 37° C. with 5% CO2/95% air in DMEM supplemented with 10% heat inactivated calf serum (CS), 4.5 mg/ml glucose, 2 mM glutamine, 100 IU/ml penicillin and 100 μg/ml streptomycin. For BOSC23 cells, CS was replaced by 10% heat inactivated fetal calf serum (FCS).

Cell Infection, Transfection and Selection

The packaging cell line, BOSC23, was grown as described (Pear, supra, Danos, O. et al. (1988) *Proc. Natl. Acad. Sci. USA* 85:6460–6464). Plasmid DNA's were prepared by the Qiagen procedure (Qiagen, Inc.) and transfected in BOSC23 cells using a calcium phosphate procedure (5prime:3prime, Inc.). Viral supematants from producers were harvested and filtered as described (Pear, supra, Danos, supra). All infections were carried out in the presence of 8 μg/ml Polybrene (Sigma). Viral supematants from BOSC23 were used to generate stable viral producers. Virus titers were estimated by infection and selection of NIH3T3 cells using standard calculations previously described (Pear, supra, Danos, supra). Detection of helper viruses was performed by a β-galactosidase mobilization assay as described (Pear, supra, Danos, supra). Selection was applied two days after infections. Standard concentrations (1X) of selection agents were 320 μg/ml for Hygromycin B (Calbiochem). Packaging NIH3T3 cells were selected with 1X, MDHF with ½X and BSMC with 2X concentrations.

RETROVIRUS CRE/LOX MEDIATED GENE INTEGRATION

To study the efficiency of gene integration using the Cre/lox mediated gene tranfer system described herein, the following protocol was used performed.

Figure 2:
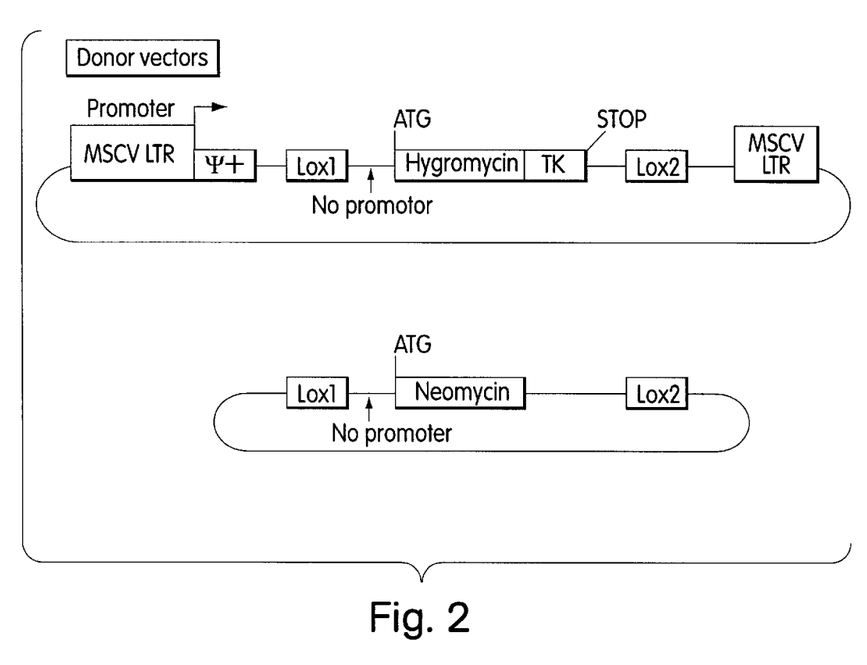
FIG. 2 is a schematic illustration of acceptor and donor vectors containing selectable marker genes and incompatible lox sequences.

Acceptor vectors were constructed using the MSCV retroviral vector. The vectors contained in order: the left MSCV LTR (containing promoter), followed by a lox L1 sequence, followed by a hygromycin-TK fusion gene (as a selectable marker), followed by a lox L2 sequence, followed by the right MSCV LTR (see FIG. 2). The retrovirus LTR was used as a the promoter for the hygromycin-TK fusion gene. Similar constructs were made using other selection markers such as neomycin.

The L1 and L2 lox sequences of the acceptor vector had the nucleotide sequences shown below (corresponding to SEQ ID NO:1 and SEQ ID NO:2). L1 is the wild type LoxP1 sequence (SEQ ID NO:1) from bacteriophage P1 (Abremski et al. (1983) *Cell* 32:1301–1311). L2 is a mutated form of the wild type LoxP1 sequence, referred to as Lox511, having a point substitution of A for G at position 7 of the eight nucleotide spacer region (Waterhouse et al. (1993) *Nucleic Acids Res.* 21(9):2265–2266).

```
              SPACER
L1 ATAACTTCGTATA ATGTATGC TATACGAAGTTAT   (SEQ ID NO:1)
L2 ATAACTTCGTATA ATGTATAC TATACGAAGTTAT   (SEQ ID NO:2)
```

Following construction of the acceptor vector ("L1-hygromycin-TK-L2 construct"), BOSC23 cells (ecotropic packaging cells) were transiently transfected with acceptor vector using a calcium phosphate procedure (5prime:3prime, Inc.). Viral supernatants from producers were harvested and filtered as described (Pear, supra, Danos, supra). All infections were carried out in the presence of 8 μg/ml Polybrene (Sigma) Viral supernatant containing high-titer ($>10^5$ pfu/ml) retroviral vector was then used to infect host NIH3T3 cells using the same procedures. After 48 hours in culture, the infected 3T3 cells were selected with hygromycin.

Donor vectors were constructed using pUC 19 plasmid (Yanish-Perron et al. (1985) *Gene* 33:103–119) as the backbone. The vectors contained in order: the L1 lox sequence, followed by a promoterless neomycin gene, followed by the L2 lox sequence (see FIG. 2). Similar donor vectors were made using hygromycin-TK, CD24, and B-globin genes in place of the neomycin gene. Control donor vectors were constructed using a neomycin gene with the PGK (phosphoglycerol kinase) promoter, PGK-neomycin.

Various concentrations of donor vector containing neomycin gene were co-electroporated, along with an expression vector containing the Cre recombinase gene, into the infected 3T3 cells. The concentrations of donor vector ranged from 10 μg to 200 μg. After 48 hours in culture, transformed cells were selected with neomycin. Concentrations 100 μg or more of donor vector resulted in a 10–30% integration efficiency (as measured by transfer of neomycin gene for hygromycin gene).

Different ratios of donor vector and Cre expression vector, ranging from 20:1 to 1:1 were co-electroporated into the infected 3T3 cells. All ratios resulted in the transfer of the neomycin for the hygromycin. However, a ratio of 3:1 (donor:Cre) resulted in the highest integration efficiency.

Figure 3:
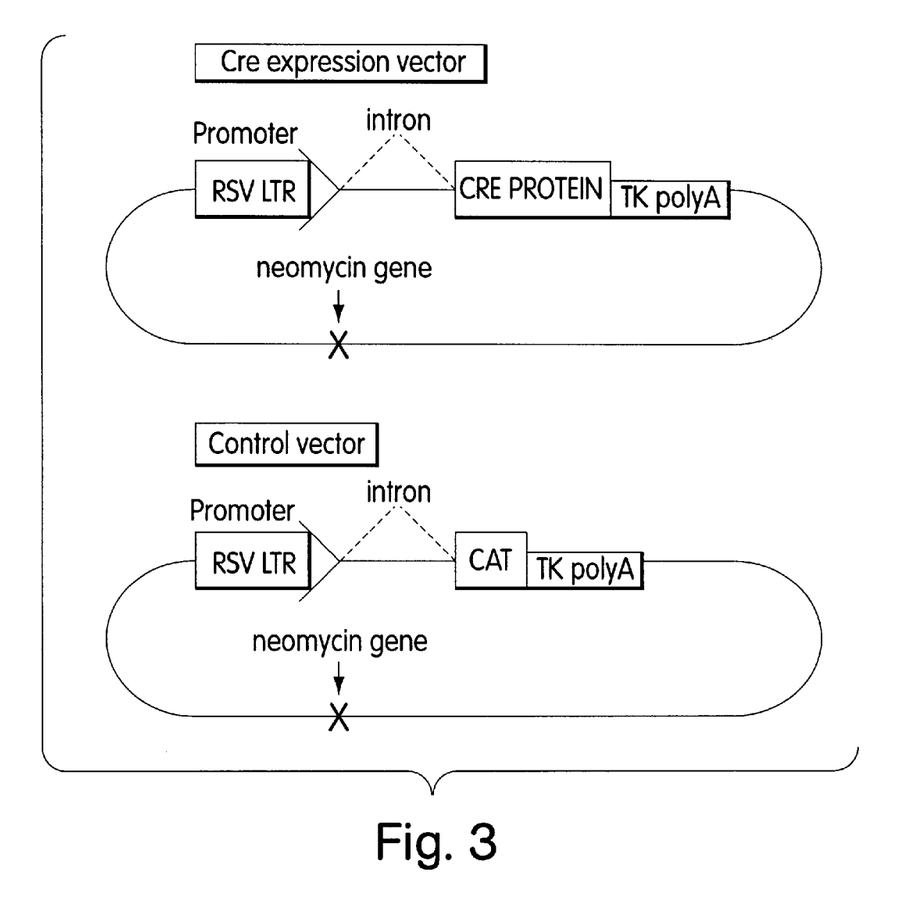
FIG. 3 is a schematic illustration of a Cre expression vector and a control Cre expression vector.

The following table provides the results of neomycin gene integration using various donor and Cre expression vectors (see FIG. 3) at a concentration of 100 μg of donor vector (DNA) at a ratio of 3 parts donor vector to 1 part Cre expression vector. Experiments E#1–4 were performed as negative controls. E#5 was the positive control.

|  | Cells Electroporated | Constructs Used | # Colonies (out of $10^7$ cells) |
| --- | --- | --- | --- |
| E#1 | 3T3 | lox 1-PGKNeo-lox 2 & control Cre expression vector | 530 |
| E#2 | 3T3 | lox 1-Neo-lox 2 & control Cre expression vector | 10 |
| E#3 | 3T3 | lox 1-Neo-lox 2 & Cre expression vector | 2 |

| Cells Electroporated | Constructs Used | # Colonies (out of 10⁷ cells) |
|---|---|---|
| E#4 | 3T3 containing lox A-hygro-TK-lox B | lox 1-Neo-lox 2 & control Cre expression vector | 21 |
| E#5 | same | lox 1-Neo-iox 2 & Cre expression vector | confluent (>10⁵) |

E#1 used the control donor vector (see FIG. 2), lox 1-PGKNeo-lox 2 (containing the neomycin gene and a promoter) along with a control Cre expression vector (see FIG. 3) (in which the sequence encoding Cre had been deleted and replaced by a gene encoding CAT). Host cells did not contain integrated acceptor vector. Therefore, E#1 demonstrated the amount of neomycin resistance conferred by random integration of the L1-PGKNeo-L2 vector capable of expressing the neomycin gene. As expected, the conferred neomycin resistance was in the range of efficiency of integration obtained by electroporation (e.g., about 0.1% efficiency).

E#2 used donor vector (promoterless) with a control Cre expression vector. Host cells did not contain integrated acceptor vector. Therefore, E#2 demonstrated the resistance conferred in the absence of acceptor vector or Cre recombinase (i.e., in the absence of efficient recombination and gene transfer). As expected, this was very low.

E#3 used donor vector (promoterless) with a functional Cre expression vector. Host cells did not contain integrated acceptor vector. Therefore, E#3 demonstrated the resistance conferred in the absence of acceptor vector (i.e., in the absence of efficient recombination and gene transfer), but in the presence of Cre recombinase. As expected, this was very low.

E#4 used donor vector (promoterless) with a control Cre expression vector (no Cre expression). Host cells contained integrated acceptor vector (L1-hygro-TK-L2). Therefore, E#4 demonstrated the gene transfer efficiency from donor vector to acceptor vector in the absence of Cre). As expected, this was very low.

E#5 used donor vector (promoterless) with a functional Cre expression vector. Host cells contained integrated acceptor vector (L1-hygro-TK-L2). Therefore, E#5 demonstrated the gene transfer efficiency from donor vector to acceptor vector in the presence of Cre. As shown in the table above, the host cells became confluent, demonstrating a greater than 1000 fold increase in gene transfer efficiency and stability.

Conclusion:

Overall, these results demonstrate that the retroviral Cre/lox mediated gene transfer system of the present invention can be used for highly efficient and stable integration of transgenes into chromosomal DNA of mammalian cells.

What is claimed is:

1. A method of causing site-specific recombination in a mammalian cell comprising contacting a recombinase with (a) an acceptor vector which is integrated into the genome of said mammalian cell, said acceptor vector comprising two lox sequences, L1 and L2, which can not recombine with one another, and (b) a donor vector which is not integrated into the genome of said mammalian cell, said donor vector being present in an amount in excess of said integrated acceptor vector, wherein said donor vector comprises a selected DNA flanked by the same L1 and L2 sequences contained in the acceptor vector, or sequences which can recombine with these L1 and L2 sequences, thereby causing transfer of the selected DNA from the donor vector into the acceptor vector by recombination at the L1 and L2 sequences.

2. The method of claim 1 wherein the acceptor vector is selected from the group consisting of retroviral vectors and adeno-associated vectors.

3. The method of claim 1 wherein L1 and L2 differ by one or more point mutations in their spacer sequences.

4. The method of claim 1 wherein L1 and L2 comprise the LoxP1 and Lox511 nucleotide sequences (SEQ ID NOS:1 and 2), respectively, and the recombinase is Cre.

5. The method of claim 1 wherein acceptor vector is a retroviral vector.

6. A method of transforming a cell with a selected DNA comprising, in any order, the steps of:

(a) introducing into the cell an acceptor vector which integrates into the genome of the cell, the acceptor vector comprising two incompatible lox sequences, L1 and L2, which can not recombine with one another;

(b) introducing into the cell a donor vector comprising the selected DNA flanked by the same L1 and L2 sequences contained in the acceptor vector or sequences which can recombine with these L1 and L2 sequences, wherein said donor vector is introduced in an amount in excess of said acceptor vector; and (c) contacting L1 and L2 with Cre, thereby causing transfer of the selected DNA from the donor vector into the acceptor vector.

7. The method of claim 6 wherein the acceptor vector is an adeno-associated viral vector.

8. The method of claim 6 wherein L1 and L2 differ by at least one nucleotide addition, deletion or substitution in their spacer sequences.

9. The method of claim 6 wherein either L1 or L2 comprises the LoxP1 nucleotide sequence (SEQ ID NO: 1).

10. The method of claim 6 wherein either L1 or L2 comprises the Lox511 nucleotide sequence (SEQ ID NO:2).

11. The method of claim 6 wherein L1 and L2 comprise the LoxP1 and Lox511 nucleotide sequences (SEQ ID NOS:1 and 2), respectively.

12. The method of claim 6 wherein L1 and L2 have the same orientation.

13. The method of claim 6 further comprising the step of introducing into the cell a gene encoding Cre recombinase.

14. The method of claim 13 wherein the gene encoding Cre recombinase is contained in an expression vector.

15. The method of claim 13 wherein the gene encoding Cre recombinase is contained in either the acceptor vector or the donor vector.

16. The method of claim 6 wherein the donor vector is introduced into the cell by electroporation.

17. The method of claim 13 wherein both the donor vector and the gene encoding Cre recombinase are introduced into the cell by electroporation.

18. The method of claim 6 wherein the selected DNA is a transgene encoding a therapeutic protein.

19. The method of claim 18 wherein the protein is β-globin.

20. The method of claim 6 wherein the donor vector, acceptor vector, or both the donor and acceptor vectors further comprise a selectable marker gene.

21. A Cre/lox mediated gene transfer system comprising:

(a) an acceptor vector which can integrate into the genome of a host cell, the acceptor vector comprising two lox sequences, L1 and L2, which can not recombine with one another;

(b) a donor vector comprising a transgene flanked by the same L1 and L2 sequences contained in the acceptor vector, or sequences which can recombine with these L1 and L2 sequences; and (c) a transient expression vector encoding a recombinase which can catalyze recombination at the L1 and L2 sequences.

22. The system of claim 21 wherein the acceptor vector is selected from the group consisting of a retroviral vector and an adeno-associated vector.

23. The system of claim 21 wherein L1 and L2 differ by one or more point mutations in their spacer sequences.

24. The system of claim 21 wherein L1 and L2 comprise the LoxP1 and Lox511 nucleotide sequences (SEQ ID NOS:1 and 2), respectively.

* * * * *

UNITED STATES PATENT AND TRADEMARK OFFICE
CERTIFICATE OF CORRECTION

PATENT NO.       : 5,928,914
APPLICATION NO.  : 08/743796
DATED            : July 27, 1999
INVENTOR(S)      : Leboulch et al.

Page 1 of 1

It is certified that error appears in the above-identified patent and that said Letters Patent is hereby corrected as shown below:

Column 1, line 3 insert the following:

--This invention was made with government support under Grant Number HL055435 awarded by the National Institutes of Health. The government has certain rights in this invention.--

Signed and Sealed this
Twentieth Day of March, 2012

David J. Kappos
*Director of the United States Patent and Trademark Office*